United States Patent
Lee

(10) Patent No.: US 9,623,060 B2
(45) Date of Patent: Apr. 18, 2017

(54) CEREAL CONTAINING HERICIUM ERINACEUM AND METHOD FOR MAKING SAME

(71) Applicant: Dae-Hee Lee, Cheongju-si (KR)

(72) Inventor: Dae-Hee Lee, Cheongju-si (KR)

( * ) Notice: Subject to any disclaimer, the term of this patent is extended or adjusted under 35 U.S.C. 154(b) by 0 days.

(21) Appl. No.: 14/785,849

(22) PCT Filed: Feb. 27, 2014

(86) PCT No.: PCT/KR2014/001636
§ 371 (c)(1),
(2) Date: Oct. 20, 2015

(87) PCT Pub. No.: WO2014/175545
PCT Pub. Date: Oct. 30, 2014

(65) Prior Publication Data
US 2016/0089406 A1  Mar. 31, 2016

(30) Foreign Application Priority Data

Apr. 26, 2013 (KR) ........................ 10-2013-0046424

(51) Int. Cl.
| | |
|---|---|
| A61K 36/07 | (2006.01) |
| A23L 7/10 | (2016.01) |
| A23L 7/122 | (2016.01) |
| A23L 7/135 | (2016.01) |
| A23L 31/00 | (2016.01) |
| A23L 33/10 | (2016.01) |

(52) U.S. Cl.
CPC .............. *A61K 36/07* (2013.01); *A23L 7/101* (2016.08); *A23L 7/122* (2016.08); *A23L 7/135* (2016.08); *A23L 31/00* (2016.08); *A23L 33/10* (2016.08); *A23V 2002/00* (2013.01)

(58) Field of Classification Search
None
See application file for complete search history.

(56) References Cited

FOREIGN PATENT DOCUMENTS

| | | | |
|---|---|---|---|
| JP | 10-511545 | A | 11/1998 |
| JP | 2000166499 | A | 6/2000 |
| JP | 2005-198576 | A | 7/2005 |
| JP | 2008-115108 | A | 5/2008 |
| JP | 2008-531063 | A | 8/2008 |
| JP | 2010-235463 | A | 10/2010 |
| KR | 1020010069431 | A | 7/2001 |
| KR | 1020080063456 | A | 7/2008 |
| KR | 100899531 | B1 | 5/2009 |
| KR | 1020100108112 | A | 10/2010 |
| WO | 2004032646 | A2 | 4/2004 |

OTHER PUBLICATIONS

International Search Report for PCT/KR2014/001636 mailed on Jun. 16, 2014.
Database search results dated Jul. 9, 2003 for "Fungus food and its production method contains high nutrient components, and has the functions of prolonging life, resisting cancer and resisting senility, and is suitable for middle-aged and old people", corresponding to XP-002755257, 9 pages.
European Search Report mailed on Mar. 23, 2016 corresponding to European Patent Application No. 14789067.7.

*Primary Examiner* — Brian J Gangle
(74) *Attorney, Agent, or Firm* — Hauptman Ham, LLP

(57) ABSTRACT

The present invention relates to a *Hericium erinaceus*-containing cereal comprising grain or legume, saccharide and *Hericium erinaceus*, and a method for preparing the same. The *Hericium erinaceus*-containing cereal according to the present invention enables the *Hericium erinaceus* component having excellent anticancer and brain function-activating effects to be naturally taken as a meal replacement or a light meal by people of all ages and both sexes without rejection.

14 Claims, No Drawings

CEREAL CONTAINING HERICIUM ERINACEUM AND METHOD FOR MAKING SAME

CROSS REFERENCE TO RELATED APPLICATION

This application claims the priority of Korean Patent Application No. 10-2013-0046424, filed on Apr. 26, 2013 in the KIPO (Korean Intellectual Property Office). Further, this application is the National Phase application of International Application No. PCT/KR2014/001636 filed Feb. 27, 2014, which designates the United States and was published in Korean.

TECHNICAL FIELD

The present invention relates to a cereal containing *Hericium erinaceus* and a method for preparing the same.

BACKGROUND ART

*Hericium erinaceus* contains many kinds of active polysaccharides compared to normal mushrooms. Particularly, it contains special active polysaccharides such as galactoxyloglucan and mannoglucoxylane, and thus has excellent anticancer activity. It has a hetero β-D-glucan content of 34.4 g/100 g, which is at least three times higher than that of *Agaricus blazei*, and thus activates the immune function of the human body to inhibit cancer cell proliferation, and the high anticancer effect of active β-D-glucan was already demonstrated by mouse experiments. In addition, it was found that the *Hericium* polysaccharide known to be contained only in *Hericium erinaceus* acts to enhance macrophages or lymphocytes by attacking bacteria, viruses or defective cells, thereby preventing the development of colorectal cancer or gastric cancer, and is also effective against various gastritis diseases. It is known that *Hericium erinaceus* contains a large amount of oleanolic acid which is contained only in some medicinal mushrooms, and thus it protects the wall of the stomach and is effective against gastric ulcer and gastritis. Particularly, it was found that *Hericium erinaceus* contains hericenone D and erinacine C, which promote the biosynthesis of nerve growth factor. It is known that nerve growth factor has an excellent effect on the prevention and treatment of senile dementia. Kawagishi et al. (Japan) extracted a physiologically active substance from *Hericium erinaceus* and identified the structure thereof, and these reported that the substance is nerve growth factor and can be used for regeneration of the central nervous system and as a therapeutic agent against dementia. In addition, there was a report of a study indicating that direct injection of nerve growth factor into the brains of Alzheimer's disease patients improved several functions including memory. However, because the blood-brain barrier, an entrance into the brain, cannot pass large molecules like nerve growth factor, nerve growth factor cannot reach the brain when it is administered orally or injected into the arm or the like. However, hericenone D and erinacine C, which are contained in *Hericium erinaceus*, can be delivered to the brain through blood to promote the synthesis of nerve growth factor, thereby providing an effective treatment method. In addition, hericenone D and erinacine C have nerve growth factor-stimulating activity four times higher than the hormone epinephrine in the brain, and thus prevent the loss of neurons and stimulate the synthesis of neurons, suggesting that these play a great role in the development of intelligence of children in the growth phase or teenagers. Particularly, minerals such as potassium, calcium, magnesium, etc., contained in *Hericium erinaceus*, enter the body and interact with enzymes and release ionized metabolic signals. According to these signals, low-molecular-weight substances such as peptides are absorbed into cells to restore the function of beta cells and promote the secretion of insulin. In other words, it is known that, through such a series of actions, insulin is normally secreted and blood glucose levels are lowered to alleviate diabetes, and the liver function is also improved. It is known that the enzyme superoxide dismutase (SOD) is contained in *Hericium erinaceus* in a large amount of 8,900 units/g and has the effects of preventing cell oxide, aging and cancer and making cells younger. In addition, according to the report of the International Medicinal Mushroom Research Society (Waseda Publishing Co., Ltd., 8-5-3 Nishi Shinjuku, Shinjuku-ku, Tokyo, Japan), *Hericium erinaceus* is effective against circulatory system diseases (hypertension, hypotension, angina, myocardial infarction, thrombotic diseases, arteriosclerosis, pneumonia, leukemia, malignant lymphoma, septicemia, etc.), digestive system diseases (duodenal ulcer, hepatomegaly, chronic gastritis, gastric ulcer, hepatocirrhosis, hepatitis B, viral hepatitis, constipation, stomatitis, pimples, piles, alveolar pyorrhea, renal failure, etc.), endocrine system diseases (allergy, diabetes, hypercholesterolemia, etc.), cerebral nervous system diseases (rheumatism, autonomic imbalance, neurosis, etc.), respiratory system diseases (chronic bronchitis, asthma, etc.), reproductive system diseases (various women's diseases, menopausal disorder, irregular menstruation, etc.), urinary system diseases (cystitis, prostatic hypertrophy, nephrosis, etc.), skin diseases (athlete's foot, eczema, atopic dermatitis, etc.), cold hypersensitivity, adhesive capsulitis, Basedows disease, pollinosis, hangover, lumbago, collagen disease, weak constitution, stiff shoulder, various eye diseases, a decline in energy, influenza, halitosis, vertigo, nausea, skin care, megrim, various swells, empyema, nasitis, rubella, etc. In addition, it was reported that the fruit body of *Hericium erinaceus* contains various physiologically active substances including hercenines (Kawagishi et al. 1990) and also contains antimicrobial substances against pathogenic microorganisms (Anke, 1977; Kuwahara et al, 1992; Kim, d. m, 2000). For internal application, *Hericium erinaceus* having the above-described effects is processed directly, or boiled, or made into powders, pills, extracts or various mixed liquids.

As described above, the various effects of *Hericium erinaceus* were already found in many literatures, but regular taking of *Hericium erinaceus* is not easy. It is complicated and difficult for general people to purchase *Hericium erinaceus* and boil or process the purchased mushroom for eating, and for this reason, processing companies make *Hericium erinaceus* into pills, extracts or powders and market the products. However, if *Hericium erinaceus* is made into pills or extracts, it can be difficult to take the pills or extracts, due to their strong fragrance, and if *Hericium erinaceus* is made into powders, the powders should be taken together with liquid such as water, and it will be very complicated and difficult to handle the powders, because the powders are fine. Particularly, when children are allowed to eat these products because of their excellent effect of activating the brain function, they show rejection, because the products are thought to be drugs.

DISCLOSURE

Technical Problem

It is an object of the present invention to provide a *Hericium erinaceus*-containing cereal comprising grain or legume, saccharide and *Hericium erinaceus*, and a method for preparing the same.

However, an object to be accomplished by the present invention is not limited to the above-mentioned object, and other objects not mentioned will be clearly understood by those skilled in the art from the following description.

Technical Solution

The present invention provides a *Hericium erinaceus*-containing cereal comprising grain or legume, saccharide and *Hericium erinaceus*.

In an embodiment of the present invention, there is provided a method for preparing a cereal containing *Hericium erinaceus*, the method comprising the steps of: (a) preparing *Hericium erinaceus*; (b) adding the *Hericium erinaceus* prepared in step (a), saccharide and water to grain or legume powder to obtain a mixture, kneading the mixture to obtain a dough, and extruding the dough; and (c) heating the dough extruded in step (b).

In another embodiment of the present invention, there is provided a method for preparing a cereal containing *Hericium erinaceus*, the method comprising the steps of: (a) preparing *Hericium erinaceus*; (b) adding saccharide and water to grain or legume powder to prepare a mixture, kneading the mixture to obtain a dough, and extruding the dough; (c) heating the dough extruded in step (b), thereby preparing a cereal; (d) coating the surface of the prepared cereal with a composition prepared by mixing the *Hericium erinaceus* prepared in step (a) with saccharide, a thickener and water; and (e) drying the cereal coated with the composition in step (d).

Advantageous Effects

The *Hericium erinaceus*-containing cereal according to the present invention enables the *Hericium erinaceus* component having excellent anticancer and brain function-activating effects to be naturally taken as a meal replacement or a light meal by people of all ages and both sexes without rejection.

BEST MODE

The present inventors have conducted studies on a method enabling *Hericium erinaceus* having excellent anticancer and brain function-activating effects to be naturally taken, and as a result, have made a cereal containing *Hericium erinaceus*, thereby completing the present invention.

Hereinafter, the present invention will be described in detail.

Specifically, the present invention provides a *Hericium erinaceus*-containing cereal comprising grain or legume, saccharide and *Hericium erinaceus*.

The *Hericium erinaceus*-containing cereal according to the present invention comprises grain or legume, saccharide and *Hericium erinaceus*.

The grain may be one or more selected from the group consisting of rice, barley, brown rice, corn, oats, beans, sorghum, common millet, foxtail millet, wheat, and combinations thereof, and the legume may be one or more selected from the group consisting of Seoritae (black soybean), red beans, mung beans, Cheongtae (green soybean), Baktae (white soybean), kidney beans, Huktae (black soybean), black Indian beans, Seomoktae (small black soybean), and combinations thereof.

The saccharide may be one or more selected from the group consisting of sugar, molasses, glucose, fructose, maltose, oligosaccharide, aspartame, stevioside, and combinations thereof.

*Hericium erinaceus* that is used in the present invention has excellent anticancer and brain function-activating effects, and may be *Hericium erinaceus* powder or *Hericium erinaceus* extract.

The *Hericium erinaceus* powder is preferably contained in an amount of 0.01-50 wt %, more preferably 0.1-15 wt %, based on the total weight of the cereal, but is not limited thereto. If the content of the *Hericium erinaceus* powder is too low, there will be a problem in that the effect of the *Hericium erinaceus* component is insignificant, and if the content of the *Hericium erinaceus* powder is too high, there will be problems in that rejection is caused by the characteristic fragrance of *Hericium erinaceus* when the cereal is taken and that the cost-effectiveness of the cereal is reduced.

In addition, the *Hericium erinaceus* extract is preferably contained in an amount of 0.001-30 wt %, more preferably 0.05-20 wt %, based on the total weight of the cereal, but is not limited thereto. If the content of the *Hericium erinaceus* extract is too low, there will be a problem in that the effect of the *Hericium erinaceus* component is insignificant, and if the content of the *Hericium erinaceus* extract is too high, there will be problems in that rejection is caused by the characteristic fragrance of *Hericium erinaceus* when the cereal is taken and that the cost-effectiveness of the cereal is reduced. If the *Hericium erinaceus* extract is used at high concentration, there will be an advantage in that the *Hericium erinaceus* extract can exhibit the same effect of the *Hericium erinaceus* powder even when it is used in an amount smaller than that of the *Hericium erinaceus* powder.

The *Hericium erinaceus*-containing cereal may further comprise one or more mushrooms selected from the group consisting of *Tricholoma matsutake*, *Lentinus edodes*, *Phellinus linteus*, *Ganoderma lucidum*, *Pleurotus ostreatus*, *Pleurotus eryngii*, *Agaricus blazei*, *Grifola frondosa*, *Flammulina velutipes*, *Sparassis crispa*, *Lyophyllum ulmarium*, *Agrocybe aegerita*, *Umbilicaria esculenta*, *Lyophyllum shimeji*, *Cordyceps sinensis*, and combinations thereof.

In addition, the *Hericium erinaceus*-containing cereal may further comprise additives, including starch, dietary fiber, milk protein, soy protein, oil and fat, minerals, vitamins, etc.

The present invention also provides a method for preparing a cereal containing *Hericium erinaceus*, the method comprising the steps of:
(a) preparing *Hericium erinaceus*;
(b) adding the *Hericium erinaceus* prepared in step (a), saccharide and water to grain or legume powder to obtain a mixture, kneading the mixture to obtain a dough, and extruding the dough; and
(c) heating the dough extruded in step (b).

Step (a) is a step of preparing *Hericium erinaceus*.

The *Hericium erinaceus* in step (a) may be *Hericium erinaceus* power or *Hericium erinaceus* extract.

The *Hericium erinaceus* powder can be prepared by washing *Hericium erinaceus* clean, freezing the washed *Hericium erinaceus*, and pulverizing the frozen *Hericium erinaceus*. Alternatively, the *Hericium erinaceus* powder can be prepared by washing *Hericium erinaceus* clean, drying the washed *Hericium erinaceus* clean to a water content of 3% or less, and pulverizing the dried *Hericium erinaceus*.

The *Hericium erinaceus* extract can be prepared by washing *Hericium erinaceus* clean, and then immediately, heating and extracting the washed *Hericium erinaceus* with a solvent. Alternatively, the *Hericium erinaceus* extract can be prepared by washing *Hericium erinaceus* clean, drying the washed *Hericium erinaceus* clean to a water content of 3% or less, and either heating and extracting the dried *Hericium erinaceus* with a solvent or pulverizing the dried *Hericium erinaceus* to obtain *Hericium erinaceus* powder and heating and extracting the *Hericium erinaceus* powder with a solvent. When the *Hericium erinaceus* extract is prepared by heating and extracting the *Hericium erinaceus* powder with a solvent, the *Hericium erinaceus* powder is preferably used in an amount of 1-80 wt %, more preferably 10-50 wt %, based on the weight of the solvent, but is not limited thereto. In addition, the solvent that is used in the preparation of the *Hericium erinaceus* extract may be one or more selected from the group consisting of a $C_1$-$C_4$ lower alcohol, ethyl acetate, acetone, water, and hexane.

Furthermore, the heating and extraction may be performed at a temperature of 25° C. to 100° C., particularly 80° C. to 98° C., for 1-48 hours. After the heating and extraction, the solvent is preferably evaporated by vacuum distillation or atmospheric pressure, thereby increasing the concentration of the *Hericium erinaceus* extract. If the concentration of the *Hericium erinaceus* extract is excessively increased so that the viscosity thereof will be excessively increased or the flowability thereof will be reduced, the *Hericium erinaceus* extract cannot be maintained in a liquid state. For this reason, the solvent is preferably evaporated such that the *Hericium erinaceus* extract can be maintained at suitable viscosity and flowability.

Step (b) is a step of adding the *Hericium erinaceus* prepared in step (a), saccharide and water to grain or legume powder to obtain a mixture, kneading the mixture to obtain a dough, and extruding the dough. The grain or legume powder can be obtained by pulverization with various mills such as a pin mill, a ball mill or an attrition mill.

After the prepared *Hericium erinaceus*, saccharide and water were added to the grain or legume to obtain a mixture, the mixture may be kneaded until a dough having a water content of 20-50 wt % is prepared.

Before the kneading process, one or more mushrooms selected from the group consisting of *Tricholoma matsutake, Lentinus edodes, Phellinus linteus, Ganoderma lucidum, Pleurotus ostreatus, Pleurotus eryngii, Agaricus blazei, Grifola frondosa, Flammulina velutipes, Sparassis crispa, Lyophyllum ulmarium, Agrocybe aegerita, Umbilicaria esculenta, Lyophyllum shimeji, Cordyceps sinensis*, and combinations thereof, may further be added, or additives, including starch, dietary fiber, milk protein, soy protein, oil and fat, minerals, vitamins, etc., may further be added.

Next, the dough may be extruded through an extruder and shaped in a molding machine. Herein, the extrusion may be performed at a temperature between 150° C. and 200° C.

Step (c) is a step of heating the extruded dough.

In this step, the extruded dough is dried by heating, thereby preparing a *Hericium erinaceus* powder-containing cereal having a water content of 2-4 wt %. Herein, the heating may be performed at a temperature of 120 to 150° C.

The present invention also provides a method for preparing a cereal containing *Hericium erinaceus*, the method comprising the steps of:

(a) preparing *Hericium erinaceus*;
(b) adding saccharide and water to grain or legume powder to obtain a mixture, kneading the mixture to obtain a dough, and extruding the dough;
(c) heating the dough extruded in step (b), thereby preparing a cereal;
(d) coating the surface of the prepared cereal with a composition prepared by mixing the *Hericium erinaceus* prepared in step (a) with saccharide, a thickener and water; and
(e) drying the cereal coated with the composition in step (d).

Step (a) is a step of preparing *Hericium erinaceus*.

The *Hericium erinaceus* in step (a) may be *Hericium erinaceus* power or *Hericium erinaceus* extract.

The *Hericium erinaceus* powder can be prepared by washing *Hericium erinaceus* clean, freezing the washed *Hericium erinaceus*, and pulverizing the frozen *Hericium erinaceus*. Alternatively, the *Hericium erinaceus* powder can be prepared by washing *Hericium erinaceus* clean, drying the washed *Hericium erinaceus* clean to a water content of 3% or less, and pulverizing the dried *Hericium erinaceus*.

The *Hericium erinaceus* extract can be prepared by washing *Hericium erinaceus* clean, and then immediately, heating and extracting the washed *Hericium erinaceus* with a solvent. Alternatively, the *Hericium erinaceus* extract can be prepared by washing *Hericium erinaceus* clean, drying the washed *Hericium erinaceus* clean to a water content of 3% or less, and either heating and extracting the dried *Hericium erinaceus* with a solvent or pulverizing the dried *Hericium erinaceus* to obtain *Hericium erinaceus* powder and heating and extracting the *Hericium erinaceus* powder with a solvent. When the *Hericium erinaceus* extract is prepared by heating and extracting the *Hericium erinaceus* powder with a solvent, the *Hericium erinaceus* powder is preferably used in an amount of 1-80 wt %, more preferably 10-50 wt %, based on the weight of the solvent, but is not limited thereto. In addition, the solvent that is used in the preparation of the *Hericium erinaceus* extract may be one or more selected from the group consisting of a $C_1$-$C_4$ lower alcohol, ethyl acetate, acetone, water, and hexane.

Furthermore, the heating and extraction may be performed at a temperature between 25° C. and 100° C., particularly 80° C. to 98° C., for 1-48 hours. After the heating and extraction, the solvent is preferably evaporated by vacuum distillation or atmospheric pressure, thereby increasing the concentration of the *Hericium erinaceus* extract. If the concentration of the *Hericium erinaceus* extract is excessively increased so that the viscosity thereof will be excessively increased or the flowability thereof will be reduced, the *Hericium erinaceus* extract cannot be maintained in a liquid state. For this reason, the solvent is preferably evaporated such that the *Hericium erinaceus* extract can be maintained at suitable viscosity and flowability.

Step (b) is a step of adding the *Hericium erinaceus* prepared in step (a), saccharide and water to grain or legume powder to obtain a mixture, kneading the mixture to obtain a dough, and extruding the dough.

The grain or legume powder can be obtained by pulverization with various mills such as a pin mill, a ball mill or an attrition mill.

After the prepared *Hericium erinaceus*, saccharide and water were added to the grain or legume to obtain a mixture, the mixture may be kneaded until a dough having a water content of 20-50 wt % is prepared.

Next, the dough may be extruded through an extruder and shaped in a molding machine. Herein, the extrusion may be performed at a temperature between 150° C. and 200° C.

Step (c) is a step of heating the extruded dough, thereby preparing a cereal.

The extruded dough can be heated, thereby preparing a dried cereal. Herein, the heating may be performed at a temperature of 120 to 150° C.

Step (d) is a step of coating the surface of the prepared cereal with a composition prepared by mixing the prepared *Hericium erinaceus* with saccharide, a thickener and water.

The thickener is added in order to increase the viscosity of the composition, and may be one or more selected from the group consisting of xanthan gum, carrageenan, alginic acid, agar, pectin, locust bean gum (LBG), and combinations thereof.

In this step, one or more mushrooms selected from the group consisting of *Tricholoma matsutake, Lentinus edodes, Phellinus linteus, Ganoderma lucidum, Pleurotus ostreatus, Pleurotus eryngii, Agaricus blazei, Grifola frondosa, Flammulina velutipes, Sparassis crispa, Lyophyllum ulmarium, Agrocybe aegerita, Umbilicaria esculenta, Lyophyllum shimeji, Cordyceps sinensis*, and combinations thereof, may further be added, or additives, including starch, dietary fiber, milk protein, soy protein, oil and fat, minerals, vitamins, etc., may further be added.

The coating may be performed by various methods, including spray, screw mixing, injection or impregnation.

Step (e) is a step of drying the cereal coated with the composition.

The cereal coated with the composition can be dried, thereby preparing a *Hericium erinaceus*-containing cereal having a water content of 3-6 wt %. Herein, the drying can be performed at a temperature between 40° C. and 100° C.

The *Hericium erinaceus*-containing cereal according to the present invention enables the *Hericium erinaceus* component having excellent anticancer and brain function-activating effects to be naturally taken as a meal replacement or a light meal by people of all ages and both sexes without rejection.

Hereinafter, preferred examples are given for a better understanding of the present invention. It is to be understood, however, that these examples are for illustrative purposes only and are not intended to limit the scope of the present invention.

PREPARATION EXAMPLES (1) Preparation of *Hericium erinaceus* Powder 10 kg of *Hericium erinaceus* was washed clean, and then dried in a cylindrical stainless vacuum dryer at a temperature of 40-60° C. for 20 hours, thereby preparing dried *Hericium erinaceus* having a water content of 3% or less. The dried *Hericium erinaceus* was pulverized with a pin mill to thereby prepare *Hericium erinaceus* powder having a size of about 50 mesh.

(2) Preparation of *Hericium erinaceus* Extract 5 kg of the *Hericium erinaceus* powder prepared in Preparation Example (1) was added to a solvent mixture of 2.5 l of ethanol and 10 l of water, and heated in a 100 l stainless container equipped with a reflux container at a temperature of 90-98° C. for 24 hours. The heated solution was filtered through a nonwoven fabric filter, and then the solvent mixture was evaporated by vacuum distillation, thereby preparing 500 ml of a *Hericium erinaceus* extract as a concentrated liquid.

Example 1

Preparation of Cereal Containing *Hericium erinaceus* Powder 10 kg of rice and 2 kg of barley were pulverized with a pin mill to thereby prepare grain powder having a size of about 50-300 mesh. To the prepared grain powder, 0.3 kg of the *Hericium erinaceus* powder, prepared in Preparation Example (1), and 1 kg of sugar, were added, and the mixture was kneaded in a stainless mixer while purified water was added thereto, thereby preparing a dough having a water content of 20-50 wt %. Then, the dough was extruded through an extruder at a temperature of 150-200° C. and shaped to a size of 3-10 mm using a molding machine. The extruded dough was heated in a preheated oven at 120-150° C. for 10-20 minutes, thereby preparing a *Hericium erinaceus* powder-containing cereal having a water content of 2-4 wt %.

Example 2

Preparation of Cereal Containing *Hericium erinaceus* Extract 10 kg of rice and 2 kg of barley were pulverized with a pin mill to thereby prepare grain powder having a size of about 50-300 mesh. To the prepared grain powder, 0.2 kg of the *Hericium erinaceus* extract, prepared in Preparation Example (1), and 1 kg of sugar, were added, and the mixture was kneaded in a stainless mixer while purified water was added thereto, thereby preparing a dough having a water content of 20-50 wt %. Then, the dough was extruded through an extruder at a temperature of 150-200° C. and shaped to a size of 3-10 mm using a molding machine. The extruded dough was heated in a preheated oven at 120-150° C. for 10-20 minutes, thereby preparing a *Hericium erinaceus* extract-containing cereal having a water content of 2-4 wt %.

Example 3

Preparation of Cereal Coated with *Hericium erinaceus* Powder 10 kg of rice and 2 kg of barley were pulverized with a pin mill to thereby prepare grain powder having a size of about 50-300 mesh. To the prepared grain powder, 1 kg of sugar was added, and the mixture was kneaded in a stainless mixer while purified water was added thereto, thereby preparing a dough having a water content of 20-50 wt %. Then, the dough was extruded through an extruder at a temperature of 150-200° C. and shaped to a size of 3-10 mm using a molding machine. The extruded dough was heated in a preheated oven at 120-150° C. for 10-20 minutes, thereby preparing a cereal. The surface of the cereal was spray-coated with a mixture of 0.3 kg of the *Hericium erinaceus* powder prepared in Preparation Example (1), 0.1 kg of molasses having a soluble solid content of 2-3 wt %, and 0.1 kg of purified water containing 0.02-0.05 wt % of edible xanthan gum dissolved therein. Next, the coated cereal was dried with hot air at a temperature of 40-100° C. for 1 hour or more, thereby preparing a *Hericium erinaceus* powder-coated cereal having a water content of 3-6 wt %.

Example 4

Preparation of Cereal Coated with *Hericium erinaceus* Extract 10 kg of rice and 2 kg of barley were pulverized with a pin mill to thereby prepare grain powder having a size of about 50-300 mesh. To the prepared grain powder, 1 kg of sugar was added, and the mixture was kneaded in a stainless mixer while purified water was added thereto, thereby preparing a dough having a water content of 20-50 wt %. Then, the dough was extruded through an extruder at a temperature of 150-200° C. and shaped to a size of 3-10 mm using a molding machine. The extruded dough was heated in a preheated oven at 120-150° C. for 10-20 minutes, thereby preparing a cereal. The surface of the cereal was spray-coated with a mixture of 0.2 kg of the *Hericium erinaceus* extract prepared in Preparation Example (2), 0.1 kg of molasses having a soluble solid content of 2-3 wt %, and 0.1 kg of purified water containing 0.02-0.05 wt % of edible xanthan gum dissolved therein. Next, the coated cereal was dried with hot air at a temperature of 40-100° C. for 1 hour or more, thereby preparing a *Hericium erinaceus* extract-coated cereal having a water content of 3-6 wt %.

It was found that the *Hericium erinaceus*-containing cereals prepared in Examples 1 to 4 contain the *Hericium erinaceus* component having excellent anticancer and brain function-activating effects, and thus advantageously enables the *Hericium erinaceus* component to be naturally taken as a meal replacement or a light meal by people of all ages and both sexes without rejection.

While the present invention has been described with reference to the particular illustrative embodiments, it will be understood by those skilled in the art to which the present invention pertains that the present invention can be easily embodied in other specific forms without departing from the technical spirit or essential characteristics of the present invention. Therefore, the embodiments described above are considered to be illustrative in all respects and not restrictive.

The invention claimed is:

1. A *Hericium erinaceus* extract-containing cereal comprising:
   grain or legume;
   saccharide; and
   *Hericium erinaceus* extract,
   wherein the *Hericium erinaceus* extract is prepared by heating and extracting dried *Hericium erinaceus* having a water content of 3% or less with a solvent mixture of ethanol and water, followed by evaporating the solvent mixture by vacuum distillation or atmospheric pressure.

2. The *Hericium erinaceus* extract-containing cereal of claim 1, wherein the *Hericium erinaceus* extract-containing cereal comprises a water content of 3-6 wt %.

3. The *Hericium erinaceus* extract-containing cereal of claim 1, wherein the *Hericium erinaceus* extract is contained in an amount of 0.001-30 wt % based on the total weight of the cereal.

4. The *Hericium erinaceus* extract-containing cereal of claim 1, further comprising one or more mushrooms selected from the group consisting of *Tricholoma matsutake, Lentinus edodes, Phellinus linteus, Ganoderma lucidum, Pleurotus ostreatus, Pleurotus eryngii, Agaricus blazei, Grifola frondosa, Flammulina velutipes, Sparassis crispa, Lyophyllum ulmarium, Agrocybe aegerita, Umbilicaria esculenta, Lyophyllum shimeji* and *Cordyceps sinensis*.

5. A method for preparing a cereal containing *Hericium erinaceus* extract, the method comprising the steps of:
   (a) preparing a *Hericium erinaceus* extract which is in a form of a concentrated liquid by heating and extracting dried *Hericium erinaceus* having a water content of 3% or less with a solvent mixture of ethanol and water, followed by evaporating the solvent mixture by vacuum distillation or atmospheric pressure thereby increasing the concentration of the *Hericium erinaceus* extract;
   (b) adding the *Hericium erinaceus* extract prepared in step (a), saccharide and water to grain or legume powder to obtain a mixture, kneading the mixture to obtain a dough, and extruding the dough; and
   (c) preparing a *Hericium erinaceus* extract-containing cereal by heating the dough extruded in step (b).

6. The method of claim 5, wherein the *Hericium erinaceus* extract-containing cereal comprises a water content of 3-6 wt %.

7. The method of claim 5,
   wherein the *Hericium erinaceus* extract is prepared by the heating and extracting *Hericium erinaceus* powder with a solvent, and
   wherein the kneading of the step (b) is performed to obtain the dough having a water content of 20-50 wt %.

8. The method of claim 5, wherein the dried *Hericium erinaceus* powder is used in an amount of 1 wt % to 80 wt % against weight of the solvent mixture.

9. The method of claim 5, wherein the heating and extracting is performed at a temperature between 25° C. and 100° C. for 1-48 hours.

10. A method for preparing a cereal containing *Hericium erinaceus* extract, the method comprising the steps of:
    (a) preparing *Hericium erinaceus* extract which is in a form of a concentrated liquid by heating and extracting dried *Hericium erinaceus* having a water content of 3% or less with a solvent mixture of ethanol and water, followed by evaporating the solvent mixture by vacuum distillation or atmospheric pressure thereby increasing the concentration of the *Hericium erinaceus* extract;
    (b) adding saccharide and water to grain or legume powder to obtain a mixture, kneading the mixture to obtain a dough, and extruding the dough;
    (c) heating the dough extruded in step (b), thereby preparing a cereal;
    (d) coating a surface of the prepared cereal with a composition prepared by mixing the *Hericium erinaceus* extract prepared in step (a) with saccharide, a thickener and water; and
    (e) drying the cereal coated with the composition in step (d).

11. The method of claim 10, wherein the *Hericium erinaceus* extract-containing cereal comprises a water content of 3-6 wt %.

12. The method of claim 10, wherein the kneading of the step (b) is performed to obtain the dough having a water content of 20-50 wt %.

13. The method of claim 10, wherein the dried *Hericium erinaceus* is used in an amount of 1 wt % to 80 wt % against weight of the solvent mixture.

14. The method of claim 10, wherein the heating and extracting is performed at a temperature between 25° C. and 100° C. for 1-48 hours.

* * * * *